(12) United States Patent
Hein et al.

(10) Patent No.: US 7,631,765 B2
(45) Date of Patent: Dec. 15, 2009

(54) SKIN TESTING-DEVICE SYSTEM

(75) Inventors: Gary L. Hein, Oakley, IL (US); Douglas S. Hein, Decatur, IL (US)

(73) Assignee: Lincoln Diagnostics, Inc., Decatur, IL (US)

( * ) Notice: Subject to any disclaimer, the term of this patent is extended or adjusted under 35 U.S.C. 154(b) by 181 days.

(21) Appl. No.: 11/951,922

(22) Filed: Dec. 6, 2007

(65) Prior Publication Data
US 2008/0073242 A1 Mar. 27, 2008

Related U.S. Application Data

(62) Division of application No. 11/449,264, filed on Jun. 8, 2006.

(51) Int. Cl.
*B65D 73/00* (2006.01)
(52) U.S. Cl. .............. 206/569; 206/470
(58) Field of Classification Search ........... 206/569, 206/443, 446, 461, 467, 470, 471, 803, 822
See application file for complete search history.

(56) References Cited

U.S. PATENT DOCUMENTS

| | | | |
|---|---|---|---|
| 2,522,309 A | 9/1950 | Simon | |
| 3,121,492 A | 2/1964 | De Paul et al. | |
| 3,145,841 A | 8/1964 | McGuire | |
| 3,390,783 A | 7/1968 | Quackenbush | |
| 3,675,766 A | 7/1972 | Rosenthal | |
| 3,695,503 A | 10/1972 | Mascetti, Jr. | |
| 3,707,227 A | 12/1972 | Britt | |
| 3,802,844 A | 4/1974 | Sendra et al. | |
| 3,923,160 A | 12/1975 | Hirano et al. | |
| D247,822 S | 5/1978 | Hein et al. | |
| 4,237,906 A | 12/1980 | Havstad et al. | |
| D276,071 S | 10/1984 | Malinoff | |
| D282,208 S | 1/1986 | Lowry | |
| D288,279 S | 2/1987 | Holewinski et al. | |
| D288,481 S | 2/1987 | Holewinski et al. | |
| D288,484 S | 2/1987 | Mitchell | |
| 4,676,377 A | 6/1987 | Rainin et al. | |
| 4,863,023 A | 9/1989 | Payne et al. | |
| 4,886,165 A | 12/1989 | Annett | |

(Continued)

FOREIGN PATENT DOCUMENTS

WO 8300296 2/1983

*Primary Examiner*—Jacob K Ackun, Jr.
(74) *Attorney, Agent, or Firm*—Banner & Witcoff, Ltd.

(57) ABSTRACT

Embodiments of the invention are directed to a skin testing-device system. The system includes a tray, a well holder that snaps into the tray and that holds a plurality of rows of test-solution wells, and a well holder-assembly lid that snaps into the tray over the well holder. The well-holder may include see-through windows such that a test-solution level is visible for substantially each of the test-solution wells from one or more single viewpoints, which may be elevated, and offset, from the well holder. The well holder-assembly lid may include areas that prevent skin-test devices in the test-solution wells from being dislodged from the test-solution wells while the well holder-assembly lid is snapped into the tray. Embodiments of the invention are directed to a clamshell-package system for holding skin-test devices. The system includes a clamshell package having generally crescent-shaped receptacles in an offset pattern and a clamshell-package lid.

5 Claims, 11 Drawing Sheets

U.S. PATENT DOCUMENTS

| | | |
|---|---|---|
| D316,146 S | 4/1991 | Payne et al. |
| 5,096,672 A | 3/1992 | Tervamaki et al. |
| 5,110,556 A | 5/1992 | Lyman et al. |
| 5,128,105 A | 7/1992 | Berthold et al. |
| 5,154,181 A | 10/1992 | Fishman |
| 5,232,094 A | 8/1993 | Fagnant et al. |
| 5,358,113 A * | 10/1994 | Hellenbrand ................. 206/411 |
| 5,447,232 A * | 9/1995 | Chow ......................... 206/378 |
| 5,514,343 A | 5/1996 | Verwohlt et al. |
| 5,588,441 A | 12/1996 | Fishman |
| 5,749,836 A | 5/1998 | Hsiao |
| 5,792,071 A | 8/1998 | Hein |
| 5,890,594 A * | 4/1999 | Hansen et al. ............... 206/472 |
| 5,931,794 A | 8/1999 | Pitesky |
| D419,441 S | 1/2000 | Gaffney et al. |
| 6,019,225 A | 2/2000 | Kalmakis et al. |
| 6,024,706 A | 2/2000 | Hsiao |
| D428,657 S | 7/2000 | Ward |
| 6,258,041 B1 | 7/2001 | Pitesky |
| D466,219 S | 11/2002 | Wynschenk et al. |
| 6,554,777 B1 | 4/2003 | Hein, Jr. |
| 6,581,777 B2 * | 6/2003 | Thibault ..................... 206/780 |
| 6,905,014 B2 | 6/2005 | Eldin |
| 6,920,980 B2 * | 7/2005 | Hwang et al. ................ 206/470 |
| 7,404,487 B2 * | 7/2008 | Kumakura et al. .......... 206/469 |
| 2003/0042170 A1 * | 3/2003 | Bolanos ..................... 206/570 |
| 2005/0007525 A1 | 1/2005 | Casanovas |
| 2005/0043648 A1 | 2/2005 | Niklasson |

* cited by examiner

SKIN TESTING-DEVICE SYSTEM

This application claims priority to and is a divisional of U.S. application Ser. No. 11/449,264 ("Skin Testing-Device System"), filed Jun. 8, 2006.

BACKGROUND

Embodiments of the invention relate, generally, to a skin testing-device system of the type commonly used for applying test solutions, such as liquid antigens used in skin testing for allergies, to patients' skin via skin-test devices that have sharp pointed ends.

The person conducting such skin testing may apply a relatively large number of test solutions (e.g., approximately 80 test solutions), one at a time, to a patient's skin. To perform skin tests of this type, the person conducting the skin test typically removes the skin-test devices, with a small amount of test solution adhering to the sharp pointed ends, from each test-solution well and applies the test solution to a site on the patient's skin in a predetermined sequence.

BRIEF SUMMARY

This Brief Summary is provided to introduce a selection of concepts in a simplified form that are further described below in the Detailed Description. This Brief Summary is not intended to identify key features or essential features of the claimed subject matter, nor is it intended to be used as an aid in determining the scope of the claimed subject matter.

Embodiments of the invention are directed to a skin testing-device system. The system includes a tray, a well holder that snaps into the tray and that holds a plurality of rows of test-solution wells, and a well holder-assembly lid that snaps into the tray over the well holder. The well-holder may include see-through windows such that a test-solution level is visible for substantially each of the test-solution wells from one or more single viewpoints, which may be elevated, and offset from, the well holder. The well holder-assembly lid may include areas that prevent skin-test devices in the test-solution wells from being dislodged from the test-solution wells while the well holder-assembly lid is snapped into the tray. Embodiments of the invention are directed to a clamshell-package system for holding skin-test devices. The system includes a clamshell package having generally crescent-shaped receptacles in an offset pattern and a clamshell-package lid.

BRIEF DESCRIPTION OF THE DRAWINGS

The foregoing Brief Summary, as well as the following Detailed Description, is better understood when read in conjunction with the accompanying drawings, which are included by way of example, and not by way of limitation, with regard to the claimed invention.

DETAILED DESCRIPTION

I. Skin Testing-device System

A. Well Holder Assembly and Lid

Figure 1:
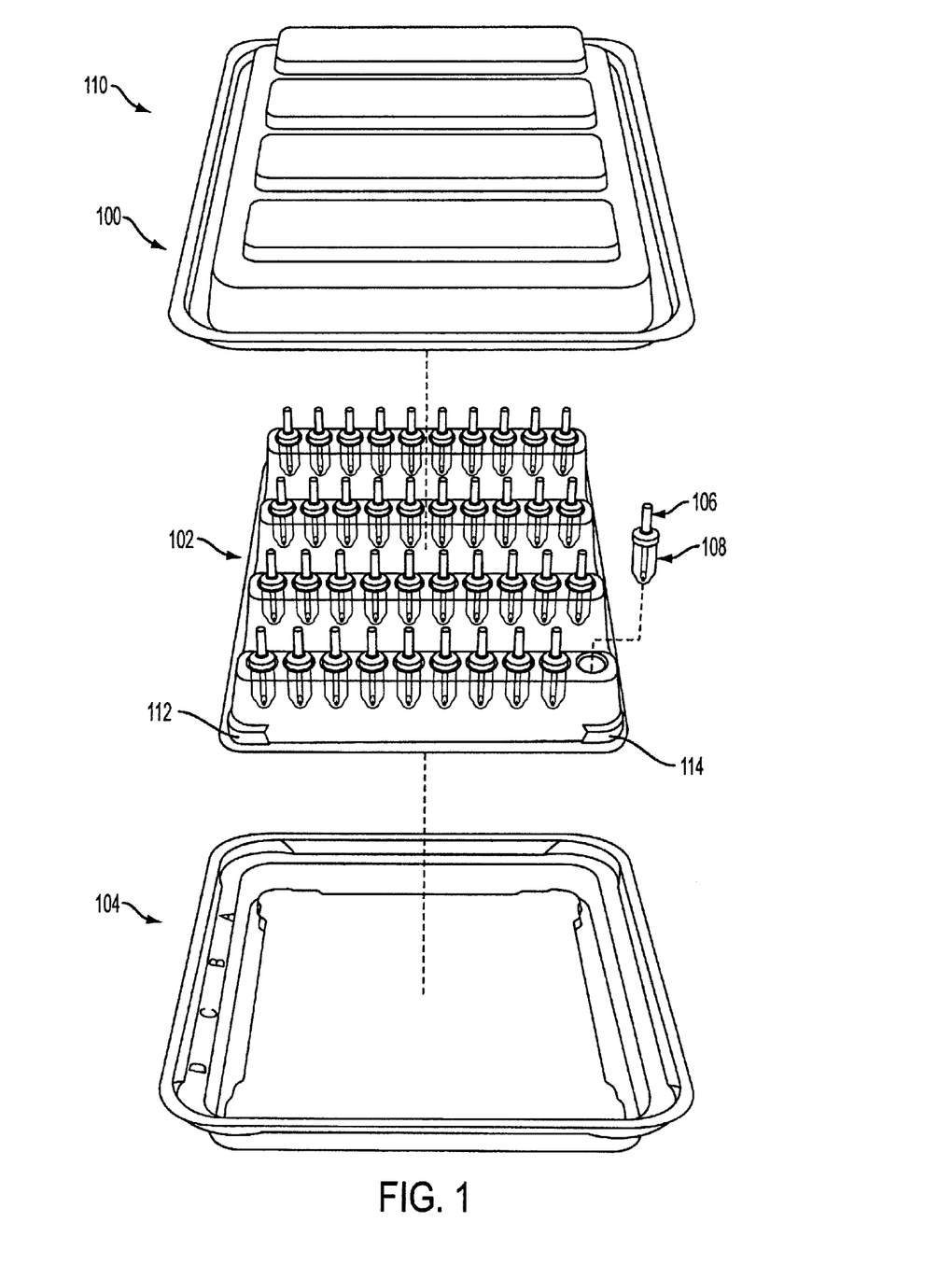
FIG. 1 shows an exemplary skin testing-device system with visible test-solution wells in accordance with embodiments of the invention.
Figure 3:
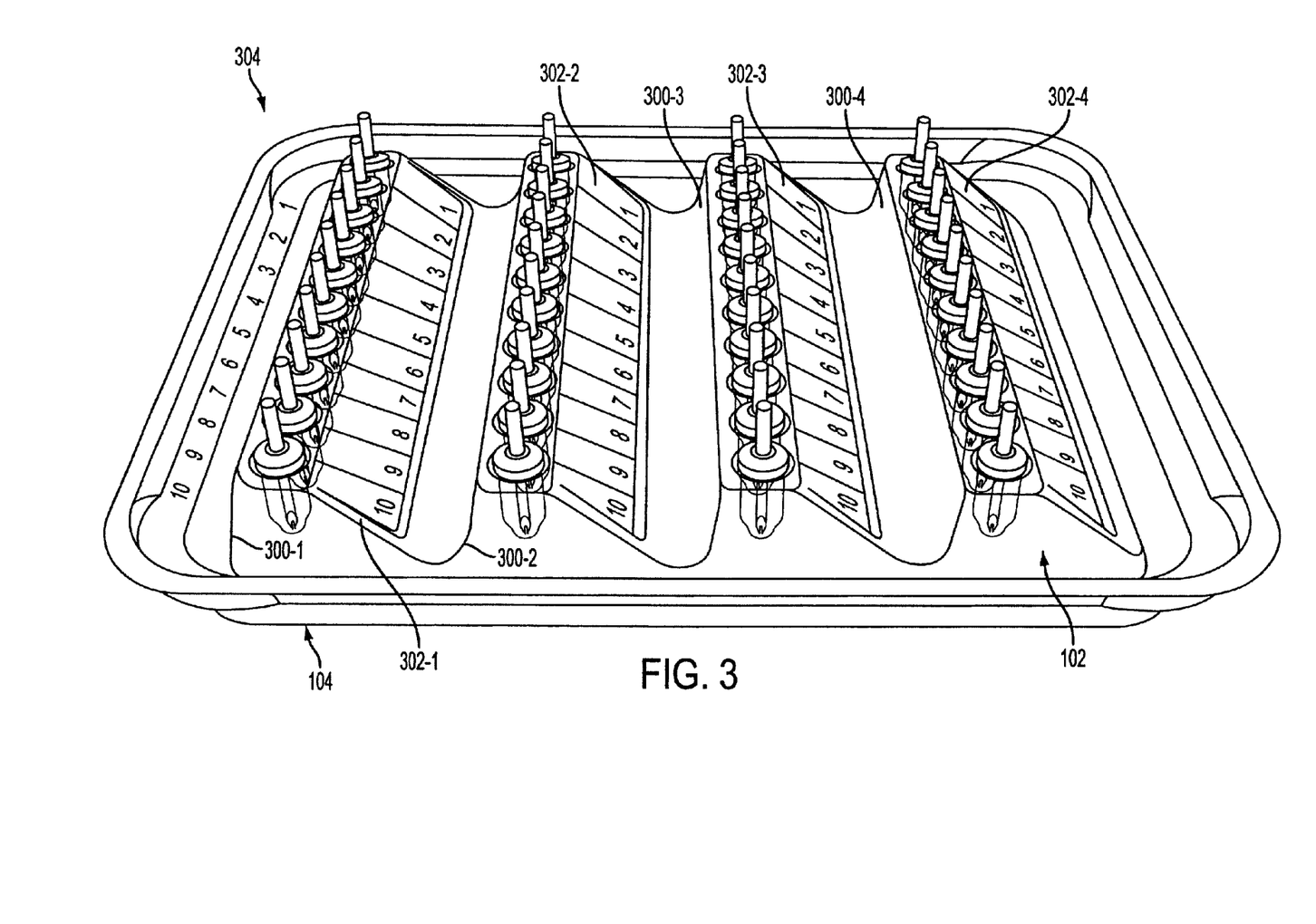
FIG. 3 is a side view of a well-holder assembly in accordance with embodiments of the invention.

FIG. 1 shows an exemplary skin testing-device system 110 with visible test-solution wells 108 in accordance with embodiments of the invention. As shown in FIG. 1, a well holder 102, which holds test-solution wells 108, which in turn hold test devices 106, snaps into a tray 104. The well holder 102 snapped into the tray 104 may be referred to collectively as a well-holder assembly 304 (FIG. 3). A well holder-assembly lid 100 may then also be snapped into the tray 104.

Figure 2:
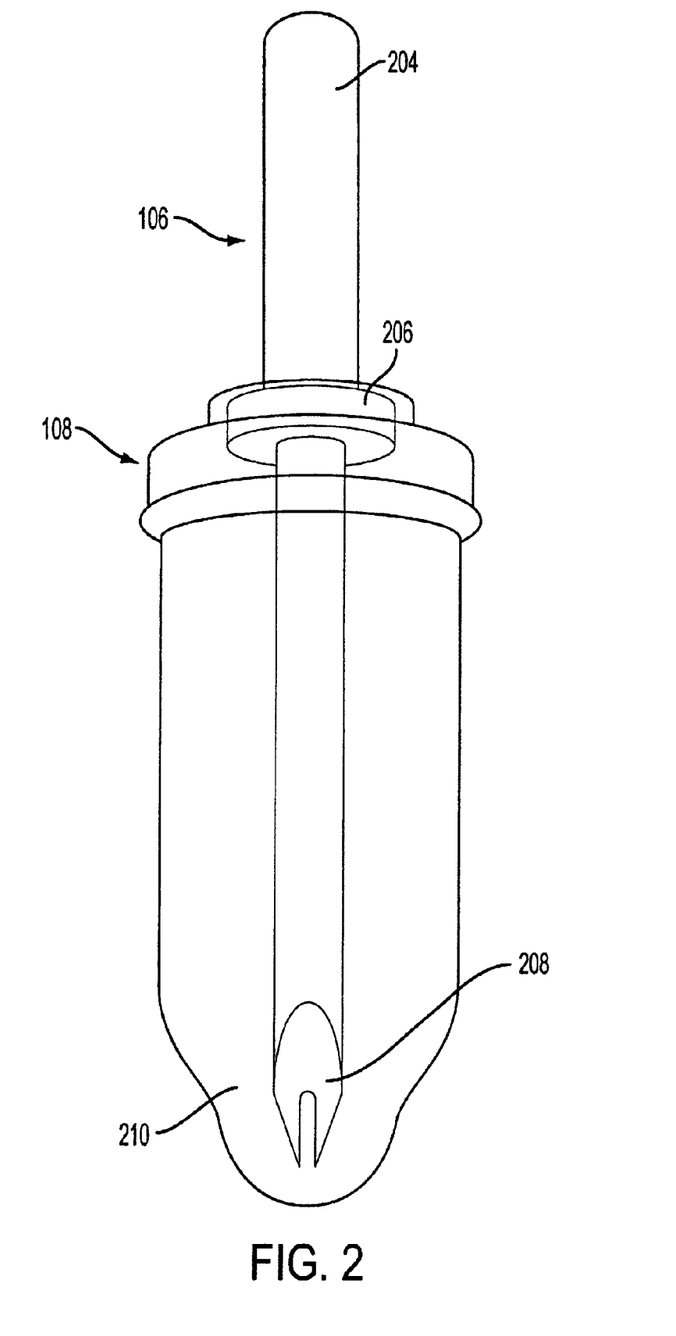
FIG. 2 shows a skin-test device in a test-solution well in accordance with embodiments of the invention.

FIG. 2 shows a skin-test device 106 in a test-solution well 108 in accordance with embodiments of the invention. Below the test device's handle 204, the skin-test device 106 includes an annular collar 206, the bottom surface of which engages an upwardly facing surface of the test-solution well 108 thereby causing the test device's bifurcated pointed end 208 to extend to an appropriate depth inside the test-solution well 108.

FIG. 3 is a side view of a well-holder assembly 304 (i.e., a well holder 102 snapped into a tray 104) in accordance with embodiments of the invention. As shown in FIG. 3, the well holder 102 includes four rows of test-solution wells. The four rows are formed by substantially vertical see-through windows 300-1 through 300-4 and slanted label sides 302-1 through 302-4. In accordance with embodiments of the invention, the well holder 102 may be made of a clear material.

In accordance with embodiments of the invention, the tray 104 may be made out of 40 gauge material, which is advantageously light weight but undesirably lacks rigidity. Once the well holder 102, which may be made of a thicker clear 60 gauge material, is snapped into the tray 104, the resulting well-holder assembly 304 is advantageously light weight, rigid, and cost effective to produce. The well holder-assembly lid 100 may also be made of clear material and, when snapped into the tray, adds additional rigidity to the skin testing-device system 110.

In accordance with embodiments of the invention, the tray 104, the well holder 102, and the well holder-assembly lid 100 may be produced from polyvinyl chloride (PVC) via thermoforming. The tray 104 may be blue and 40 gauge, while the well holder-assembly lid 100 may be clear and 40 gauge. The well holder 102 may be clear and 60 gauge. The test-solution wells 108 may be produced from clarified polypropylene via injection molding. As will be apparent, other suitable arrangements of colors, material thicknesses, and/or manufacturing processes may also be used.

Figure 4:
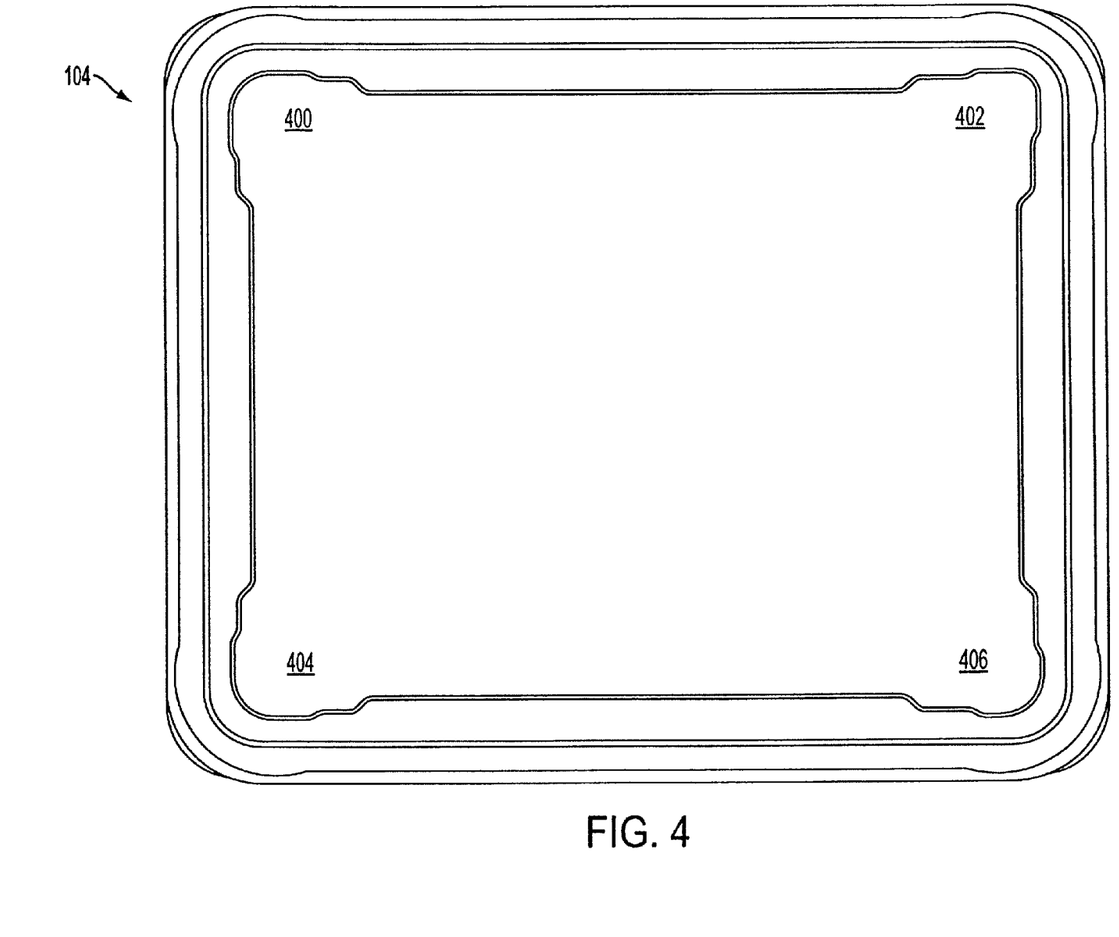
FIG. 4 is a bottom view of a tray in accordance with embodiments of the invention.

FIG. 4 is a bottom view of a tray 104 in accordance with embodiments of the invention. As shown in FIG. 4, the tray 104 includes male tray lug formations 400, 402, 404, and 406, which are formed such that the well holder 102 will fit into the tray 104 in only the correct orientation. In other words, the well holder's female well-holder receptacles 112 and 114, engage the male tray lug formations to prevent the well-holder 102 from being inserted into the tray 104 rotated 180° from its correct orientation. In this way, the labels 1-10 on the well holder 102 will match the FIGS. 1-10 on the tray 104 and letters A through D on one side of the well holder 102 will match letters A through D formed on the tray 104, which will prevent confusion from arising with respect to which test solution is in which test-solution well 108 as a result of the well holder 102 being snapped into the tray 104 in an incorrect orientation.

Figure 5:
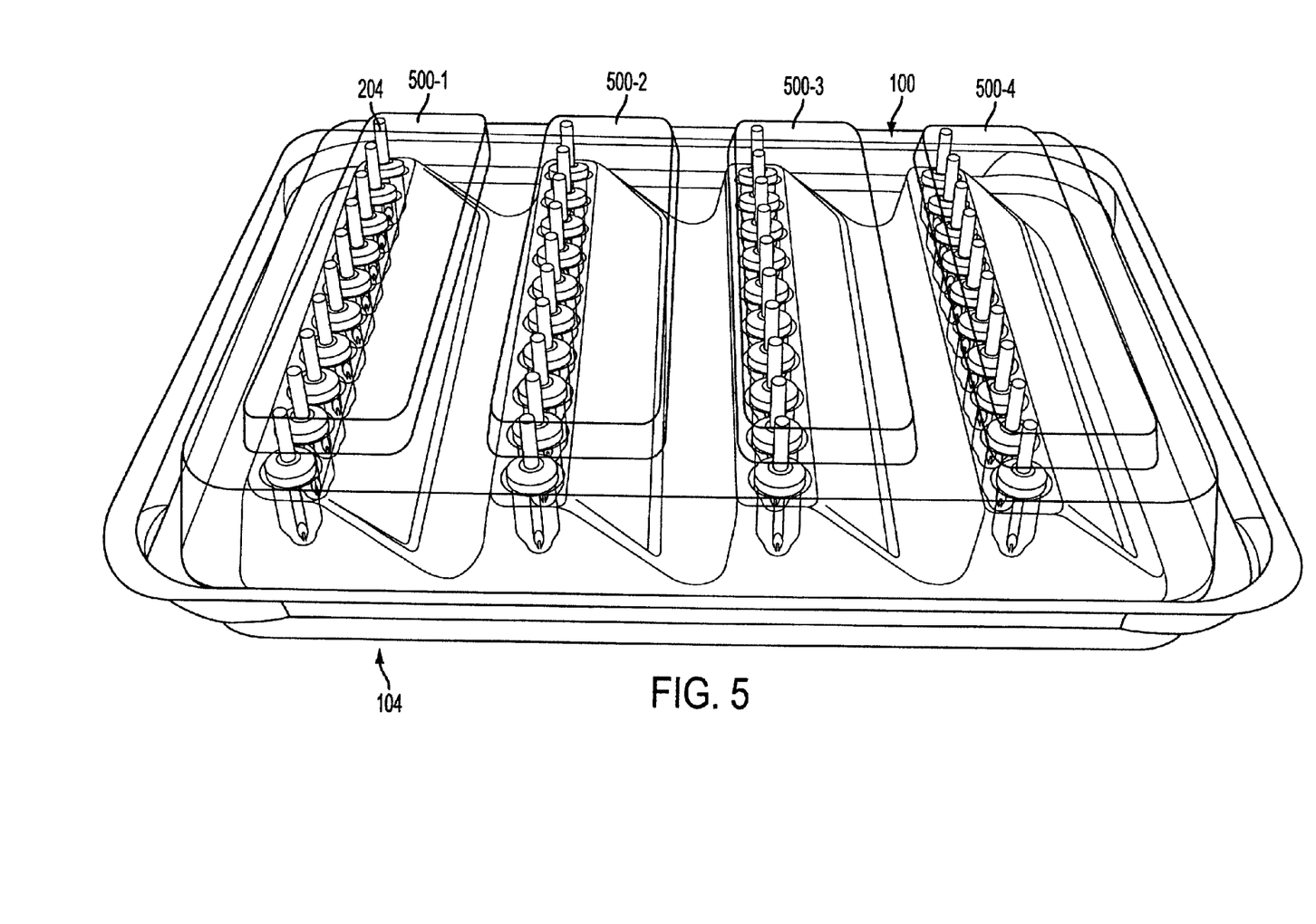
FIG. 5 is similar to FIG. 3 and includes a well holder-assembly lid.

FIG. 5 is similar to FIG. 3 and includes a well holder-assembly lid 100, which includes raised areas 500-1 through 500-4. As shown in FIG. 5, a distance between the respective tops of the test-device handles 204 and the bottom surfaces of the raised areas 500 is relatively small. In accordance with embodiments of the invention that distance is approximately 1 millimeter. As will be apparent, other suitable distances may also be used.

The relatively small distance between the respective tops of the test-device handles 204 and the bottom surfaces of the raised areas 500 advantageously prevents the test devices 106 from inadvertently falling out of the test-solution wells 108 when the tray is dropped, knocked off of a table, turned upside down, and the like.

If the skin testing-device system 110 were turned upside down with the lid on, none of the test devices 106 would come out of their respective test-solution wells 108. This is a significant functional advantage relative to conventional skin testing-device systems because it is not uncommon for a user in a hurry to drop one or more trays. With conventional trays, test devices fall out, are contaminated (i.e., are no longer sterile), and cannot be used. By keeping the test devices 106 in their respective test-solution wells 108, embodiments of the invention prevent the undesirable consequences associated with test devices falling out of conventional skin testing-device trays.

If the skin testing-device system 110 with the well holder-assembly lid 100 on was turned upside down, and there was test solution in the test-solution wells 108, some test solution would likely seep out of the test-solution wells 108. However, if a user dropped the skin testing-device system 110 on it's side or right-side up, test solution would probably not come out of the test-solution wells 108. And, if the skin testing-device system 110 fell upside down and was turned right-side up substantially right away, test solution would probably not come out of the test-solution wells 108, unless the test-solution wells 108 were overfilled.

Some users travel to satellite offices one or more days per week. When they travel, they typically take a cooler with multiple skin testing-device systems 110 loaded with test solutions. The spill-resistance provided by embodiments of the invention provides a significant functional advantage under such circumstances because, even if the user jammed on their car's brakes as hard as possible, test solution would probably not spill, and devices would not become contaminated by falling out of the skin testing-device system 110.

The raised areas 500-1 through 500-4 are configured so that it does not matter whether the lid is rotated 180°. Regardless of the lid's orientation (i.e., rotated 180° or not) relative to the well-holder assembly 304, the lid will fit over the test device handles 204, as discussed above, and will allow the skin testing-device systems 110 to stack one on top of another, as discussed below.

The raised areas 500-1 through 500-4 provide added rigidity to the well holder-assembly lid 100 thereby producing a more rigid, lighter weight, and more cost effective skin testing-device system 110 relative to a system without the raised areas 500-1 through 500-4.

Figure 6:
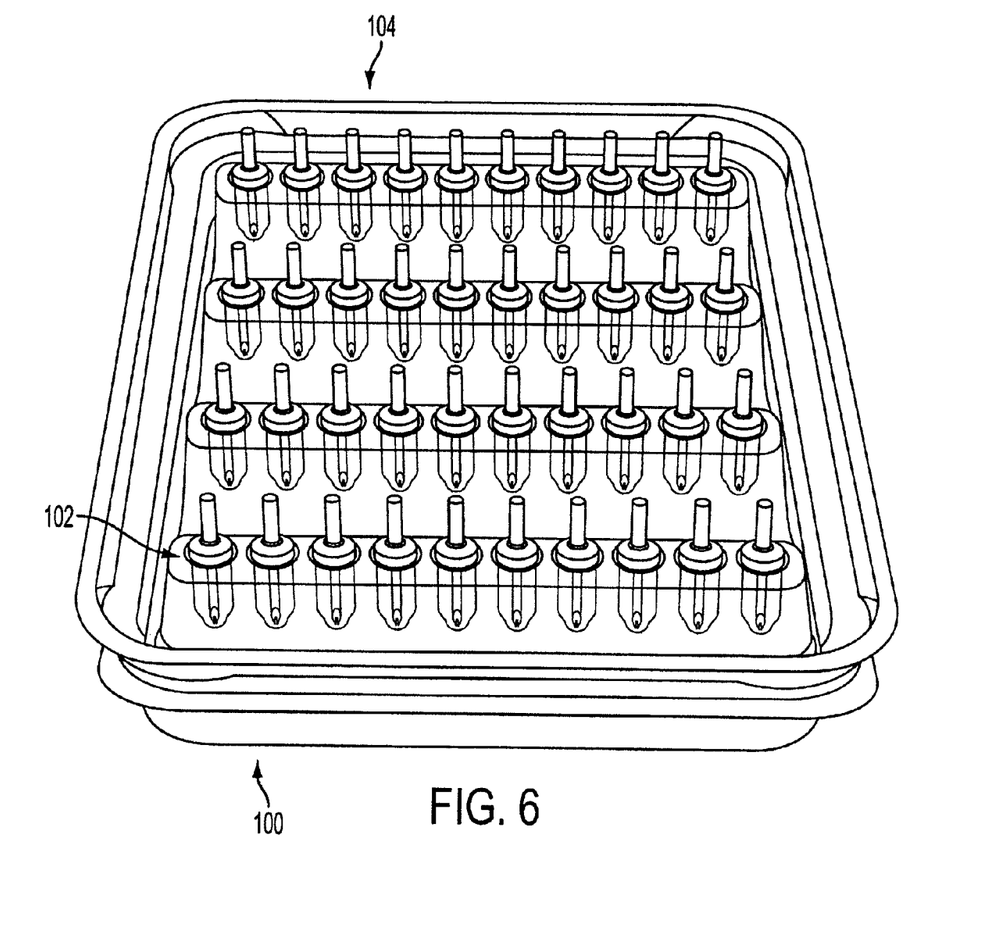
FIG. 6 shows a well holder-assembly in an upside-down well holder-assembly lid and shows how test-solution wells are visible in accordance with embodiments of the invention.

FIG. 6 shows a well holder-assembly 304 in an upside-down well holder-assembly lid 100 and shows how test-solution wells 108 are visible through see-through windows 300-1 through 300-4 in accordance with embodiments of the invention. Being able to see the respective levels of the test solutions in the test-solution wells 108 through the see-through windows 300 advantageously allows a user to determine quickly whether any test-solution wells are low enough that they should be refilled. In accordance with embodiments of the invention, a user can quickly perform a visual inspection of the test-solution levels contained in multiple rows of test-solution wells 108 from one or more single viewpoints, each of which may be elevated, and offset, from the well-holder assembly. As such, unlike the situation with conventional skin testing-device trays, there is no need to rotate, pick up, or otherwise move the well-holder assembly 304 to overcome an obstructed view of test-solution wells 108.

As shown in FIG. 2, a test-solution well 108 may contain a well reservoir 210 at the bottom of the test-solution well 108. The well reservoir 210 may contain a sufficient amount of test solution for performing a predetermined number of skin tests, such as 60 skin tests. As will be apparent, well reservoirs 210 of different suitable shapes and/or sizes may also be used such that a different amount of test solution may be contained in the well reservoir 210.

Users of conventional skin testing-device systems frequently realize, while performing a skin-test procedure, that they are using, and have already repeatedly used, test devices that have no test solution on them because the test-solution level has dropped too low such that the test device cannot pick up the test solution. Being able to see the respective levels of the test solutions in the test-solution wells 108, through the see-through windows 300, significantly reduces the likelihood of users allowing the test-solution levels to get low enough that the test device cannot pick up the test solution. In this way, embodiments of the invention provide a significant functional advantage relative to conventional skin testing-device systems.

Figure 7:
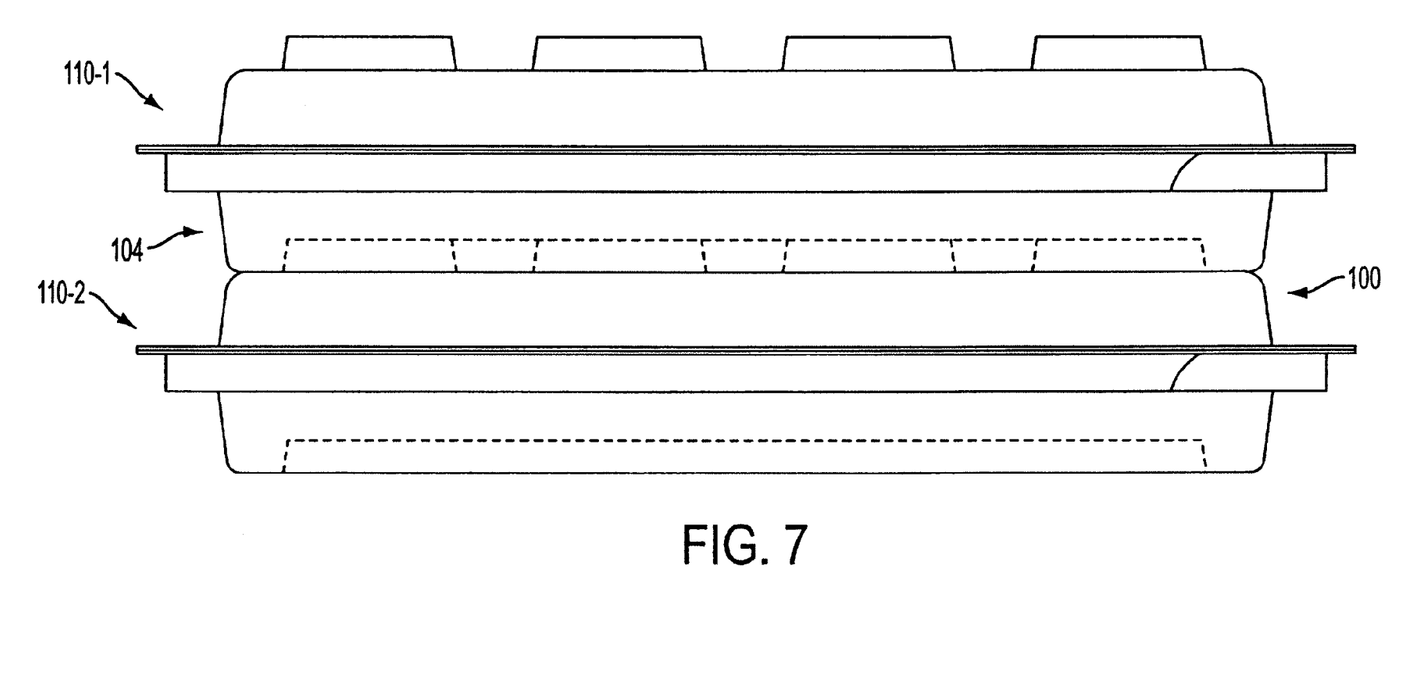
FIG. 7 shows a skin testing-device system stacked on top of a second like skin testing-device system in accordance with embodiments of the invention.

FIG. 7 shows a skin testing-device system 110-1 stacked on top of a like skin testing-device system 110-2 in accordance with embodiments of the invention. Two or three skin testing-device systems 110 stacked one on top of another may be handled easily. Most users will not exceed 80 test solutions while performing skin testing on a particular patient. So, two skin testing-device systems 110, each of which includes 40 test-solution wells, per testing station will suffice for most offices. Although the skin testing device system 110 of FIG. 1 includes 40 test-solution wells 108, other suitable numbers of test-solution wells may be used.

B. Test Device-clamshell Package

Figure 8:
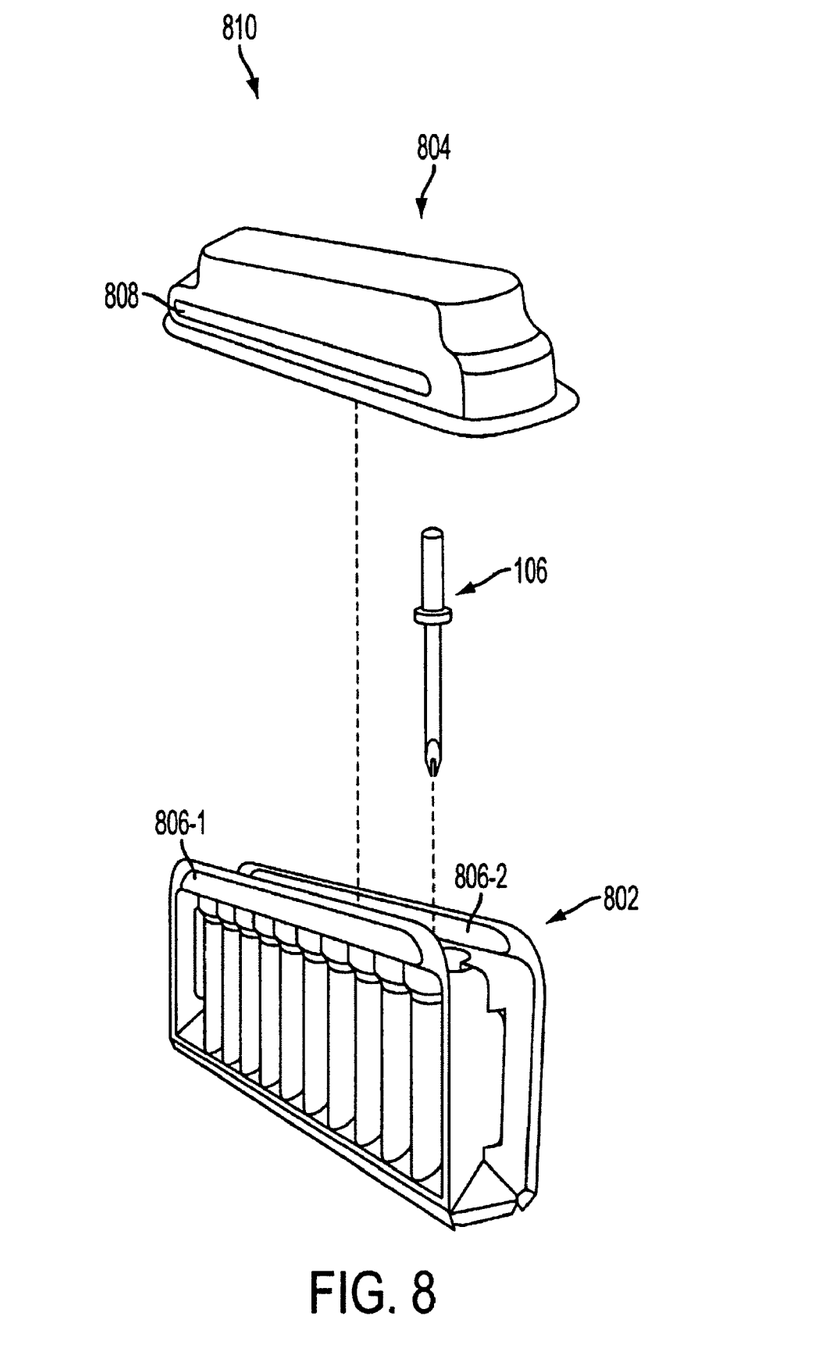
FIG. 8 shows a test-device clamshell-package system in accordance with embodiments of the invention.

FIG. 8 shows a test-device clamshell-package system 810 in accordance with embodiments of the invention. The test-device clamshell-package system 810 includes a clamshell package 802, a test device 106, and a clamshell-package lid 804. As shown in FIG. 8, the test device 106 is received in the clamshell package 802, and the clamshell-package lid 804 may be snapped onto the clamshell package 802. Male lid lugs 806-1 and 806-2 engage corresponding female lid receptacles 808, and the clamshell-package lid 804 adds rigidity to the clamshell package 802, when the clamshell-package lid 804 is snapped onto the clamshell package 802.

Figure 9:
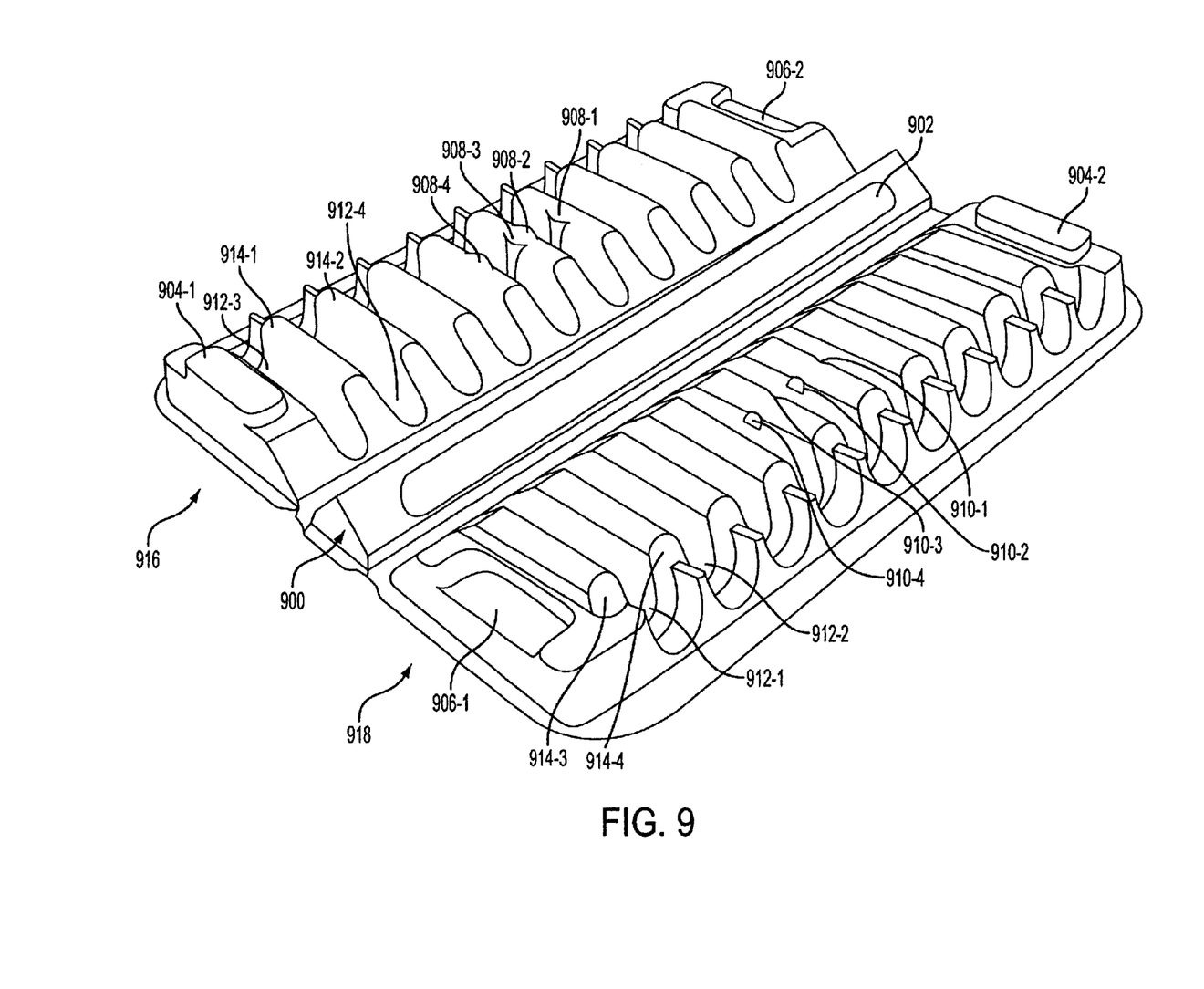
FIG. 9 shows a test device-clamshell package before its two sides are folded together in accordance with embodiments of the invention.

FIG. 9 shows a clamshell package 802 before its two sides are folded together in accordance with embodiments of the invention. As shown in FIG. 9, the clamshell package 802 includes a triangular hinge portion 900, which advantageously allows the clamshell package 802 to be formed in one piece. In accordance with embodiments of the invention, the clamshell package 802 and the clamshell-package lid 804 may be produced from clear 15 gauge polyvinyl chloride (PVC) via thermoforming. As will be apparent, other suitable arrangements of colors, material thicknesses, and/or manufacturing processes may also be used.

Figure 10:
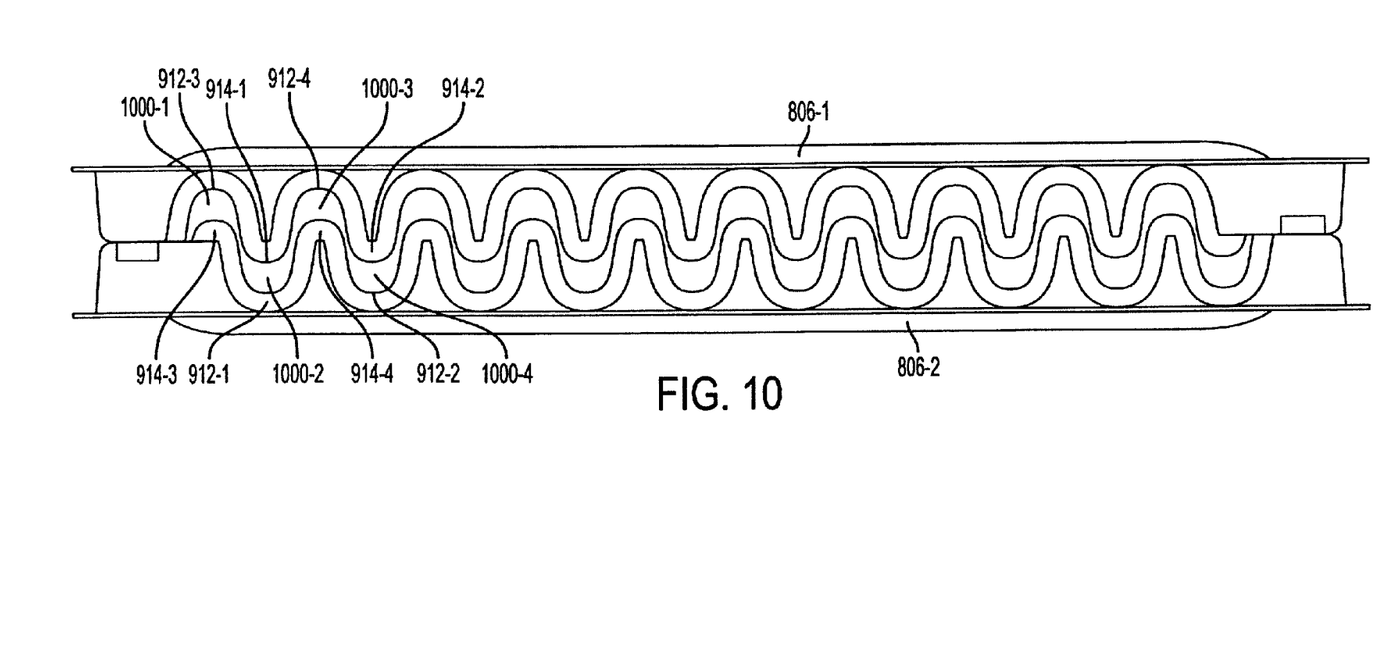
FIG. 10 is a top view of a clamshell package after its two sides are folded together in accordance with embodiments of the invention.

The triangular hinge portion 900, along with male lugs 904-1 and 904-2, central male lugs 908-1 through 908-4, female receptacles 906-1 and 906-2, and central female receptacles 910-1 through 910-4, allows the two sides 916 and 918 of the clamshell package 802 to be snapped together such that the two sides 916 and 918 fit together to form an offset pattern of test-device receptacles 1000 (FIG. 10). The male lugs 904-1 and 904-2, central male lugs 908-1 through 908-4, female receptacles 906-1 and 906-2, and central female receptacles 910-1 through 910-4 facilitate a proper fit of the two sides 916 and 918 while preventing the two sides from coming together too far and/or bowing out in the center of the two sides.

The male lugs 904-1 and 904-2, central male lugs 908-1 through 908-4, female receptacles 906-1 and 906-2, and central female receptacles 910-1 through 910-4 act as both stops as to how far the two sides 916 and 918 of the clamshell package 802 come together, and they retain the sides 916 and 918 once the lugs and receptacles engage one another. If the sides 916 and 918 of the clamshell package 802 came too far together, the test devices 106 would not go into the clamshell package. If the sides 916 and 918 of the clamshell package 802 were bowed out, the clamshell-package lid 804 would not snap onto the clamshell package 802 easily.

Each of the two sides 916 and 918 of the clamshell package 802 includes generally u-shaped female receptacle formations, such as generally u-shaped female receptacle formations 912-1 through 912-4, and generally u-shaped male receptacle formations, such as generally unshaped male receptacle formations 914-1 through 914-4.

FIG. 10 is a top view of a clamshell package 802 after its two sides are folded together in accordance with embodiments of the invention. When the two sides 916 and 918 of the clamshell package 802 are folded and snapped together, generally crescent-shaped receptacles, such as generally crescent-shaped receptacles 1000-1 through 1000-4, are formed. As shown in FIG. 10, generally crescent-shaped receptacle 1000-1 is formed by generally u-shaped female receptacle formation 912-3 and generally u-shaped male receptacle formation 914-3. Generally crescent-shaped receptacle 1000-2 is formed by generally u-shaped female receptacle formation 912-1 and generally u-shaped male receptacle formation 914-1. Generally crescent-shaped receptacle 1000-3 is formed by generally u-shaped female receptacle formation 912-4 and generally u-shaped male receptacle formation 914-4. And, generally crescent-shaped receptacle 1000-4 is formed by generally u-shaped female receptacle formation 912-2 and generally u-shaped male receptacle formation 914-2.

The offset pattern of receptacles 1000 formed by folding the two sides 916 and 918 of the clamshell package 802 together advantageously produces a relatively compact package size as compared with a similar package without the offset pattern of receptacles 1000. And the offset pattern of receptacles 1000 also makes it easier for users to take the test devices 106 out of the clamshell package 802 than it would be absent the offset patter of receptacles.

Figure 11:
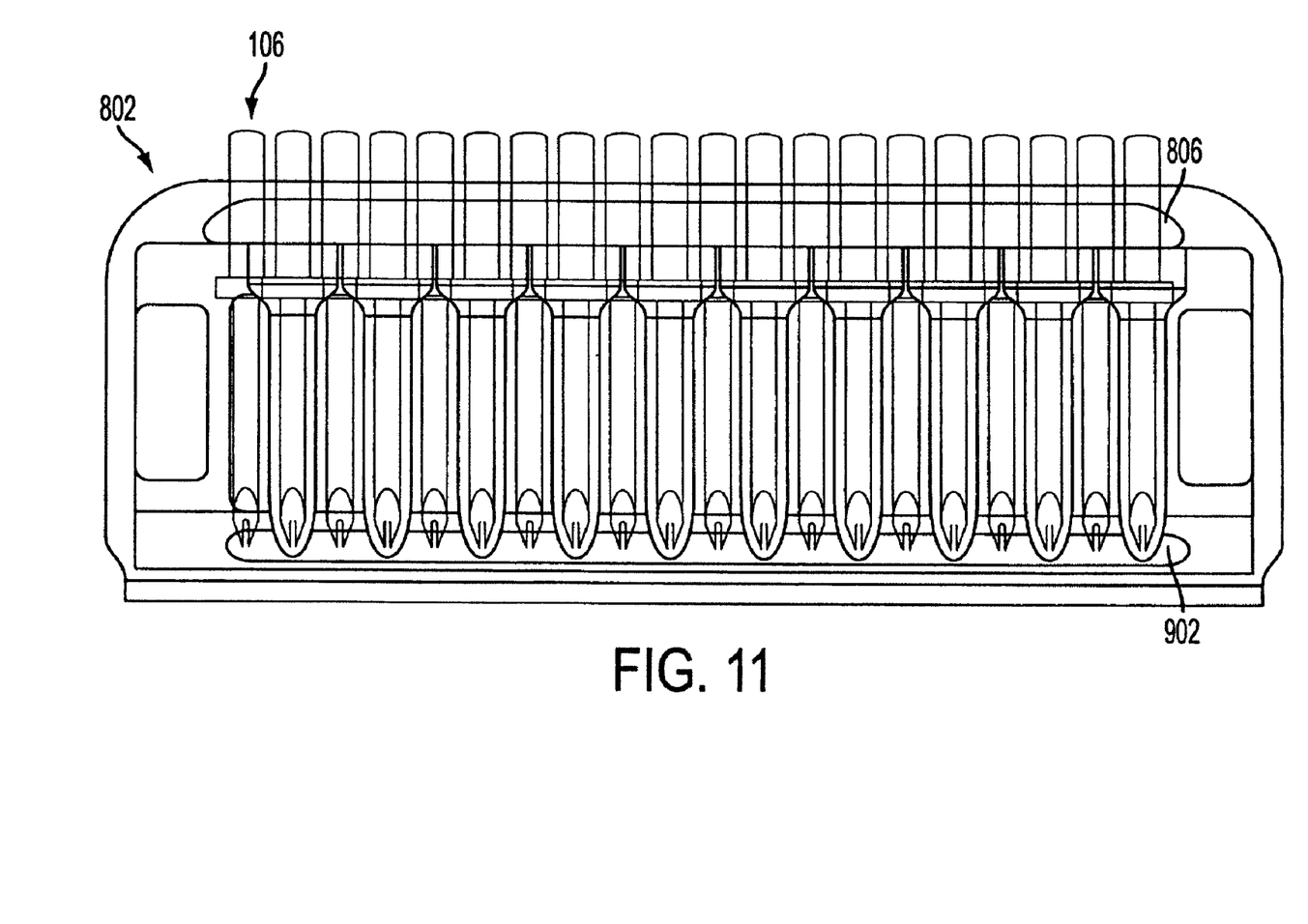
FIG. 11 is a side view of a clamshell package holding test devices in accordance with embodiments of the invention.

FIG. 11 is a side view of the clamshell package 802 holding test devices 106 in accordance with embodiments of the invention. As shown in FIG. 11, groove 902 provides additional space for the bifurcated pointed ends 208 of the test devices. This extra space prevents damage to the test devices 106 while the test devices 106 are loaded into, and held in, the clam shell package 802.

A clamshell-package system 810, in accordance with embodiments of the invention, is a departure from conventional skin-test-device packages that use a flat holder that results in a single layer of devices that lay flat and that are retained by friction on the test-device's shaft. With the conventional horizontally-oriented friction-fit arrangement, two hands are needed to remove devices from the package: one hand to hold the package, and another hand to pull the devices out sideways. The conventional arrangement allows loosely held devices to fall on the floor and get contaminated if the device holder gets tilted.

In contrast, a clamshell-package system 810, in accordance with embodiments of the invention, has an upright orientation. The upright orientation, in accordance with embodiments of the invention, does not rely on a friction fit, but relies on the test devices 106 being able to fall freely down in to the clamshell package 802 once the package has been snapped shut. Then the test devices 106 are retained by the clamshell-package lid 804, which also adds rigidity to the clamshell-package system 810. When the clamshell-package lid 804 is taken off, the test devices 106 are oriented in substantially the same direction, which facilitates unloading the test devices 106 from the clamshell package 802, which can be done with one hand, and loading the test devices 106 into the skin testing-device system 110.

VII. Concluding Remarks

Although the subject matter has been described in language specific to structural features and/or methodological acts, the subject matter defined in the appended claims is not necessarily limited to the specific features or acts described above. Rather, the specific features and acts described above are disclosed as example forms of implementing the claims.

We claim:

1. A clamshell-package system for holding skin-test devices, the system comprising:
   a clamshell package including
      a first side that includes a first plurality of u-shaped female receptacle formations and a first plurality of u-shaped male receptacle formations,
      a second side that includes a second plurality of u-shaped female receptacle formations and a second plurality of u-shaped male receptacle formations, and
      a triangular hinge portion between the first side and the second, such that, when the first side and the second side are folded together, the first plurality of u-shaped male receptacle formations are received in the second plurality of u-shaped female receptacle formations thereby creating a first plurality of generally crescent-shaped receptacles, and the second plurality of u-shaped male receptacle formations are received in the first plurality of u-shaped female receptacle formations thereby creating a second plurality of generally crescent-shaped receptacles that are offset relative to the first plurality of generally crescent-shaped receptacles; and
   a clamshell-package lid.

2. The clamshell-package system of claim 1, wherein the first side includes a first male lug and a first female receptacle, and the second side includes a second male lug and a second female receptacle such that, when the first side and the second side are folded together, the first male lug is received in the first female receptacle and the second male lug is received in the second female receptacle.

3. The clamshell-package system of claim 2, wherein the first and second sides include at least one central male lug, and at least one central female receptacle such that, when the first side and the second side are folded together, the at least one central male lug is received in the at least one central female receptacle.

4. The clamshell-package system of claim 1, wherein the triangular hinge portion contains a pair of grooves that create space to protect the pointed ends of test devices held in the clamshell package.

5. The clamshell-package system of claim 1, wherein the first and second sides of the clamshell package include a pair of male lid lugs that engage a corresponding pair of female lid receptacles of the clamshell-package lid when the clamshell package lid is snapped onto the clamshell package.

* * * * *